(12) United States Patent
Alders et al.

(10) Patent No.: US 6,320,654 B1
(45) Date of Patent: *Nov. 20, 2001

(54) METHOD FOR THE AUTOMATIC RECOGNITION OF SURFACE DEFECTS IN BODY SHELLS AND DEVICE FOR CARRYING OUT SAID METHOD

(75) Inventors: Klaus Alders, Denkendorf; Martina Lehe, Stammham; Gang Wan, Neuburg, all of (DE)

(73) Assignee: Audi AG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,786
(22) PCT Filed: Jul. 10, 1998
(86) PCT No.: PCT/EP98/04291
  § 371 Date: Jan. 13, 2000
  § 102(e) Date: Jan. 13, 2000
(87) PCT Pub. No.: WO99/04248
  PCT Pub. Date: Jan. 28, 1999

(30) Foreign Application Priority Data

Jul. 18, 1997 (DE) ............................................. 197 30 885

(51) Int. Cl.$^7$ .................................................. G01N 21/00
(52) U.S. Cl. ....................................................... 356/237.2
(58) Field of Search ................................... 356/371, 237, 356/376, 373, 374, 394, 392, 237.1, 237.2, 391, 445–448; 250/561, 562, 571, 572; 348/124

(56) References Cited

U.S. PATENT DOCUMENTS 4,792,232  12/1988  Jobe et al. ............................ 356/394
4,989,981   2/1991  Kawamura et al. .................. 356/394
5,331,169   7/1994  Tanaka et al. ........................ 250/372
5,367,378 * 11/1994  Harding et al. .
5,414,518   5/1995  Yakejian .............................. 356/376
5,546,189 *  8/1996  Svetkoff et al. .

FOREIGN PATENT DOCUMENTS 19534145    4/1996  (DE) ................................. 195/145.7
4338223     5/1994  (DE) ........................................ 21/88
4041166     6/1992  (DE) ............................. G01M/11/00
3813239    10/1990  (DE) ............................. G01N/21/88
3712513    11/1988  (DE) ................................ H04N/7/18
0286994     7/1994  (EP) .
2 308 656 A  2/1997  (GB) ............................. G01N/21/88

* cited by examiner

Primary Examiner—Frank G. Font
Assistant Examiner—Tu T Nguyen
(74) Attorney, Agent, or Firm—Lalos & Keegan

(57) ABSTRACT

In a vehicle production process, a system for detecting selected surface defects of a vehicle body prior to painting generally consisting of a conveyor operative for advancing a plurality of such vehicle bodies along a line of travel; an array of devices disposed transversely of the line of travel, operative to irradiate at the selected angles, sequential transverse sections of each of such vehicle bodies with grid patterns of light; a plurality of devices, operative to optically detect reflective grid patterns of light from the transverse sections; a computer including a processor and a database provided with files of reference data representing relevant defect surfaces of selected vehicle bodies, operative to process data generated by the detecting devices, utilizing triangulation techniques and accounting for three-dimensional phase shifts, to generate composite detected data, comparing such composite detected data with selected reference data to generate identification data representing coordinates of relevant defect surfaces of such vehicle bodies; and a substance emitting device operative in response to said identification data for marking relevant defect surfaces of such bodies.

13 Claims, 2 Drawing Sheets

METHOD FOR THE AUTOMATIC RECOGNITION OF SURFACE DEFECTS IN BODY SHELLS AND DEVICE FOR CARRYING OUT SAID METHOD

The invention relates to a process for automatic recognition of surface defects in body shells and a device for application of the process.

BACKGROUND OF THE INVENTION

In the manufacture of vehicles, body shells which are conveyed from a body shell construction line to an enameling line painting station generally have surface defects which are regarded by a customer as quality- lowering defects unless subjected to finishing operations. Consequently, such surface defects in body shells are to be detected and reworked.

In the past, relevant surface defects in series production have been recognized and evaluated subjectively by an inspector, especially by probing while wearing gloves, by display from different viewing directions and, if desired, by stripping with a whetstone if the inspector's experience has been that surface defects often occur at specific points on a body shell type.

Surface defects such as this may be dents/bulges, collapses, injection point/solder voids, uneven areas/hairline cracks, etc. The geometric parameters in evaluation are depth, extent, gradients, surface curvature, local frequencies of undulations, and positions of surface defects. Determination of whether a surface defect is relevant for a reworking operation normally depends on evaluation of a combination of the parameters indicated. For example, a dent 20 $\mu$m deep and 50 mm long can easily be recognized and must be reworked, while a dent of the same depth and 200 mm long normally is not recognized as a surface defect impairing quality and accordingly no reworking is required. Such combinations and relationships of parameters are of necessity made by an inspector in subjective evaluation, no clear-cut boundaries existing between the various relevant surface defects present resulting from such combinations.

In view of the complex and variable defect patterns indicated, automated computer recognition of such relevant surface defects has not been possible in the past.

In addition, the surface of body shells from body shell operations is often coated with a film of oil which is dull, diffused and dirty. This situation makes both subjective detection of surface defects by an inspector and automated recognition difficult. Relevant surface defects not recognized in the body shell are not recognized until after base enameling, when additional inspection is required. It is apparent that the cost of reworking surface defects is the higher the farther the body has advanced in the manufacturing process, and especially in the enameling process.

In order to reduce the high cost of recognizing relevant surface defects and of regular late reworking after base enameling, a number of attempts have already been made and experiments conducted to automate recognition of surface defects requiring reworking by measurement systems and machines, with the aim of recognizing as large a number of relevant surface defects as possible before enameling.

State-of-the-art systems, for example, involve operation by a strip projection process or on the basis of moire interferometry, in which adequate measurement accuracies of about 10 $\mu$m can be achieved by means of phase-shift processes. These processes do, however, require a time of approximately 1 minute for recognition and evaluation of an area measuring approximately 250 mm×250 mm. Such measurement processes are accordingly much too long for series production, in which a normal conveyor belt speed for body shells is about 4 meters per minute.

An alternative state-of-the-art process, called retroreflex process, has also been tested for recognition of surface defects in body shells. In this process the surface of a body shell is irradiated with a light beam. The radiation is reflected at the angle of incidence of a retroflector which is positioned perpendicularly to the surface examined. Display of surface defects is markedly intensified by multiple reflection of the light beam and so can be recognized by means of relatively simple image processing operations. A disadvantage of this process is, of course, that it is feasible only if a brightening agent is used. This brightening agent is to be applied to the surface before detection and recognition and rinsed off again after recognition. This represents a costly additional process step involving expenditure for the brightening agent. In addition, the brightening agent is a chemical harmful to the environment which creates the problem of disposal. Consequently, this process as well is to be rejected for use in series production.

The object of the invention is creation of a process for automatic recognition of surface defects requiring reworking, one suitable for series production, and of a device for application of this process.

SUMMARY OF THE INVENTION

In accordance with the present invention, a body shell is carried on a conveyor belt controlled by an optical measuring device. This optical measuring device comprises a projection device which generates a disk-shaped light tunnel as a light curtain extending more or less transversely to the direction of conveyance, through which light curtain a body shell is conveyed. A test strip of the surface positioned in a transverse plane of the body shell is irradiated.

The projection device emits a grid structure so that the test strip is correspondingly irradiated with a specific grid image made up of light and dark grid points, preferably in black and white.

The test device also comprises a camera device which records light reflected from the test strip as a representation of the grid image points at a specific angle. The position and shape of the representation of the reflected grid image of the grid points recognized by the camera device, which points regularly depict displacement and distortion relative to the grid emitted, is sent to a computer system as a test signal.

State-of-the-art triangulation methods are employed, or three-dimensional phase shifts are taken into account, in the computer system to recognize surface unevenness on the basis of the test signal.

Such surface defects are recognized as relevant ones requiring reworking through comparison with defect patterns stored in the computer.

This process is used to advantage for complete three-dimensional scanning of the surfaces of a body shell as this body shell is conveyed through the optical measuring device. The strip projection applied and evaluation of the test strip, in conjunction with a CCD camera, allow online scanning of the three-dimensional surface under operating conditions and at the conveyor speeds used in series production. A laser sweep projection process, in which a laser beam is projected onto the surface and recorded by a CCD camera (area camera or video camera), may also be used in place of normal light. A line scan camera may also be employed in a more costly solution.

This yields the advantage of making complete and accurate surface recognition before enameling possible. Such defects are preferably recognized by the proposed measuring process in body shells coming directly from body shell production, where the body surfaces to be examined are normally diffuse, of different dull colors, and often fouled. Complete and accurate recognition of surface defects before enameling greatly reduces costly reworking operations during or after the enameling process, so that on the whole higher quality is achieved at lower cost. The large volumes of data accumulated can be processed at higher body conveying speeds of up to 5 meters per minute by use of strip projection and CCD cameras.

The projection device consists preferably of a plurality of adjacent radiation emitters irradiating the continuous test strips, and the camera device of a plurality of adjacent CCD cameras recording the test strip. The radiation emitters and the CCD cameras are controlled at a distance from and at an angle to the test strip just acquired such that each of them is positioned in an interval window relative to the body outline and/or a suitable reflection angle is formed.

Such control is advantageously made possible by mounting the radiation emitters and CCD camera rotatably on lateral uprights of a gantly and by having an upper crossbeam of the gantry, which also carries radiation emitters and CCD cameras, controlled on the basis of the vertical configuration of a body shell.

It is advisable to store in the computer system a test program for each vehicle type and design, e.g., one with two doors, sliding roof, etc., a program which covers in particular the surface configuration and if desired system-dependent surface defects of this vehicle type. It is proposed that in order to initiate this test program the beginning of the body shell, along with the appropriate data from a vehicle data carrier, be transmitted to the computer system for activation of the associated test program.

The optical measuring device is used to record test data relating to surface defects, such as depth, extent, local frequency of a plurality of adjacent surface defects, and the location of the surface defects. These test data are compared with the data relating to stored defect patterns, account being taken of additional typical defect patterns in the machining process and frequencies of surface defects over time in the stored defect patterns.

Only as a result of relating and combining these data are evaluation and determination made of whether a relevant surface defect corresponding to a stored defect pattern and requiring reworking is involved. A single extreme value of the surface defects indicated above is not authoritative for determining if reworking is required.

In order to enable the computer system to select relevant surface defects, it is contemplated that surface defects recognized as relevant by an inspector be recorded by measurement means and be stored in the computer as surface defects, along with the test data in accordance with the criteria indicated above. After subjective determination of a number of surface defects by an inspector and storage of the corresponding objectively recorded data as defect patterns in the computer system, a list of defect patterns is compiled in the computer system of defect patterns which can be objectively recognized by the measuring system in conjunction with the computer system.

To make it possible to evaluate the large quantity of data accumulated in the short period available, it is proposed that the computer system be configured as a computer network consisting of a control computer, a measuring computer, and an evaluation computer linked together preferably in a network structure by fiber optic cables. It further is proposed to use software based on artificial intelligence techniques, surface defects being mapped in imprecise form, classified, and if necessary corrected. In addition, adaptive software is employed so that new defect types may be simply supplemented or configured autonomously as defect patterns in a self-adaptation process.

In an especially preferred development of the process, coordinate data acquired for surface defects recognized as being relevant are not only read out or stored but are also transmitted to a marking device downstream from the measuring device. In the latter, the surface defects are appropriately marked automatically on the body shell by way of controllable marking nozzles on the basis of the coordinate data acquired. The relevant surface defects as thus marked may then simply be reworked.

Use is made of a device for automatic recognition of surface defects in body shells in series production; this device consists of a conveyor belt for conveyance of body shells and an optical measuring system the bearing structure of which surrounds the conveying means transversely to the direction of conveyance of these conveying means.

The optical measuring device consists of a projection device consisting of radiation emitters and a camera device of CCD cameras mounted on the bearing structure and directed toward a body shell conveyable by the optical measuring device, the radiation emitters generating a disk-shaped light tunnel as a light curtain with the specified grid pattern on the surface of the body shell as a test strip. The CCD cameras record the reflected light accordingly as an image of the grid points. The device also consists of a computer system for determination and recognition of relevant surface defects requiring reworking, the computer system being linked to the radiation emitters and CCD cameras for signal transmission. A device such as this makes it possible to carry out the process indicated in the foregoing with the advantages stated. The layout of such a device may be designed so as to be relatively simple and compact.

An essential requirement for accuracy of the optical measuring process is among other things vibration-free and continuous passage of the body shell through the optical measuring device. For this purpose, it is proposed, as conveying means a continuously stable and quietly operating conveyor belt which, as stated in claim 13, may be driven on each side by a small link conveyor chain.

As bearing structure for the layout of the radiation emitters and CCD cameras, there is provided a gantry with at least two gantry uprights and an upper gantry crosspiece, this arrangement resulting in the achievement of a favorable three-dimensional and stable layout. Preference is given here to mounting of a radiation emitter and an associated CCD camera on each of the gantry uprights and a radiation emitter and an associated CCD camera in the center of the gantry crosspiece. In addition, a radiation emitter and an associated CCD camera are mounted in each area to the side of the gantry crosspiece and are set at an oblique angle to the center of the gantry. It also is contemplated the mounting of a radiation emitter and an associated CCD camera which are offset on the gantry, each at the same height and in the direction of conveyance of the body shell, in order to obtain a favorable reflection angle.

For the sake of suitable measurement spacing and reflection angles, mounting the radiation emitters and/or CCD cameras so as to be pivotable under control and/or parts of the bearing structure is proposed, preferably the gantry crosspiece, so as to be movable under control. Every actuation is effected by the test program stored in the computer system for the particular body type involved.

The device also comprises sensors, such as optical sensors, for recognition of the beginning and the position of the body shell and for acquisition of body data by way of a vehicle data carrier. Such sensors are connected to the computer system.

In an especially preferred embodiment of the device, a marking device is mounted downstream from the optical measuring device through which the conveying means also passes. The marking device comprises a bearing structure similar to that of the optical marking device, it also being in the form of a gantry with two lateral gantry uprights and at least one vertically adjustable gantry crosspiece controlled by the computer system. Mounted on the bearing structure are controlled-movement and removable marking nozzles which are charged with water-soluble paint for marking of relevant surface defects.

For the purpose of variable use of the entire device, it is provided that the conveying means and the optical measuring device and/or the marking device be designed as a self contained unit. This unit can accordingly be employed for a variety of functions in the process chain and in different manufacturing plants and is easily transported.

Since stray light may possibly distort the test results, it is contemplated that there be mounted, at least in the area of the optical measuring device, a cover surrounding this device, preferably an opaque curtain. Openings of suitable size are to be kept clear in the entrance and exit areas of the body shells.

The device is inserted preferably in the process chain between shell fine reworking and base coat enameling, if desired upstream or downstream from a washing facility. This ensures that relevant surface defects will be automatically recognized and repaired before enameling, and also that no impurities such as grinding residue, etc. will be introduced.

DETAILED DESCRIPTION OF THE INVENTION

Figure 1:
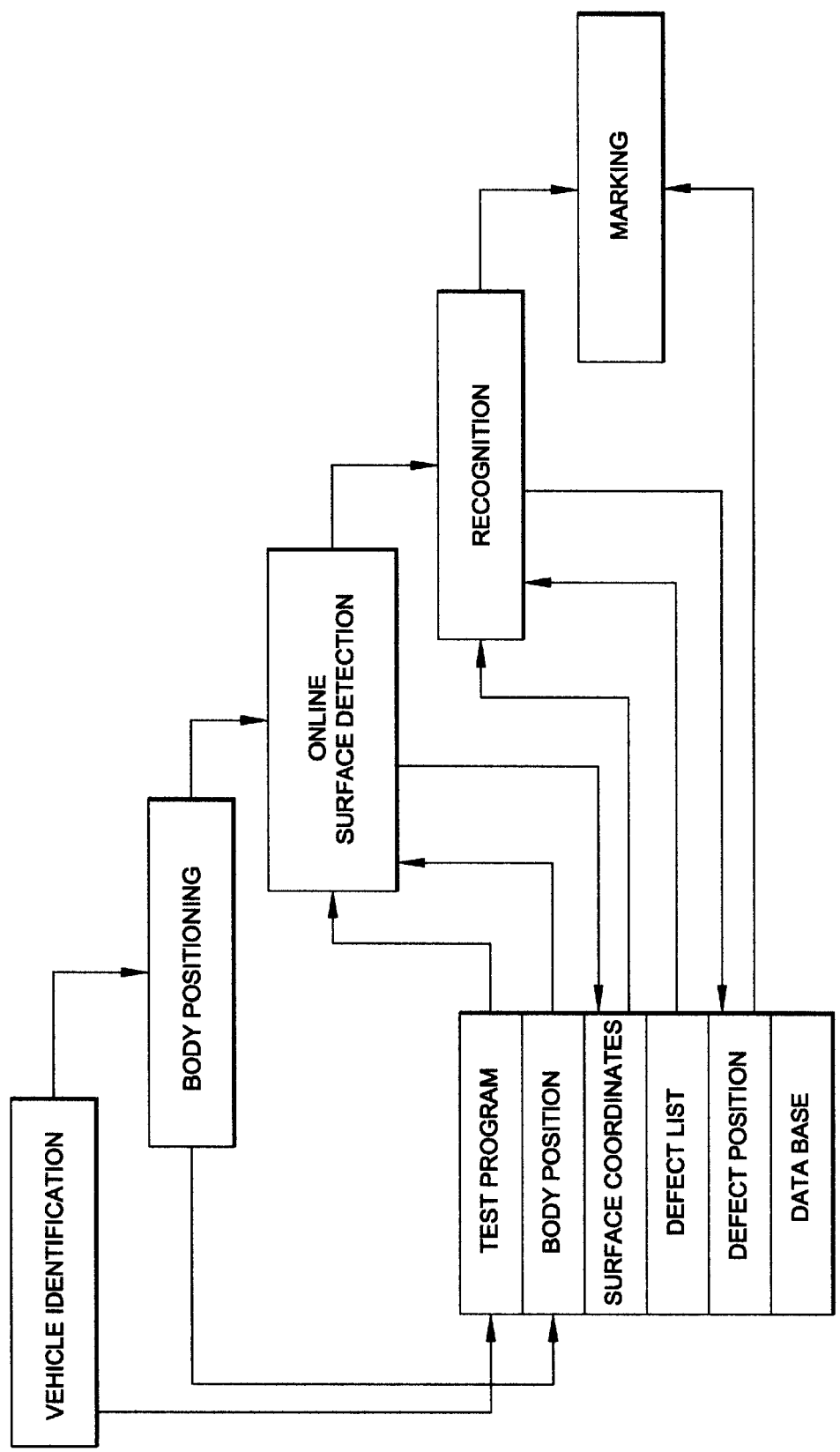
FIG. 1 shows a flow chart of the process.

FIG. 1 presents a flow chart of a process for automatic recognition of surface defects in body shells, in which a body shell is conveyed under control on conveying means by a device for application of this process.

As is to be seen from the flow chart, vehicle identification is first carried out. The body data entered on the vehicle identification data carrier fastened to the body shell relating to the pertinent vehicle type and its design are recorded by a sensor of a sensing mechanism. Then, or even at the same time as vehicle identification, another sensor of the sensing mechanism detects the front of the body shelf. Lastly, these data are transmitted to a computer system and as a result a test program for the particular vehicle type stored in the computer system is activated.

This test program is part of a data base of the computer system which has been designed as a combined control computer, measuring computer, and evaluating computer for evaluation of a large quantity of data accumulated over a brief period.

Positioning of the body is followed by online surface data acquisition. This is accomplished by means of an optical measuring device and is used for acquisition of complete data concerning the three dimensions of the surfaces of the body shell. For this purpose the optical measuring device comprises a projection device with a plurality of radiation emitters and a camera device with a plurality of CCD cameras.

Specifically, the radiation emitters generate a light tunnel acting as a light curtain and extending across the direction of conveyance through which light curtain the body shell is conveyed. In this process the radiation emitters each irradiate a test strip positioned on the surface of the body shell. The radiation emitters emit a grid structure, so that the test strip on the surface of the body shell is irradiated by a specific grid pattern of lighter and darker grid image elements. Light reflected from the irradiated test strip is recorded by the COD cameras at a specific angle as an image of the grid image elements. The position and shape of the image of the reflected grid image elements, which generally represent a displacement and distortion of the grid emitted, are entered into the computer system as a test signal.

For the purpose of obtaining suitable test distances and reflection angles, the radiation emitters and CCD cameras must each be positioned at a predetermined distance from and angle to the body outline. They are for this purpose moved by the computer system on the basis of control by the outline. Any surface unevenness may then be determined and precisely located by suitable correlated surface coordinates on the body shell, on the basis of this test signal, by already known triangulation methods if necessary with three-dimensional phase shifts taken into account.

The surface unevenness as thus determined, and accordingly establishment of whether a surface defect requiring reworking is involved, are evaluated within the framework of recognition following the online data acquisition. Comparison here with defect patterns of a list of defects stored in the computer recognizes specific surface unevennesses as surface defects requiring reworking.

Specifically, the test data on surface unevennesses acquired by the optical measuring device, such as depth, local frequency of a plurality of adjacent surface unevennesses, and the position of the surface unevennesses on the body shell, are compared with the corresponding data for the stored defect patterns. In addition, typical surface defects in the machining process and frequencies of surface defects are also taken into account in the data for stored defect patterns and thus serve as a basis for the process of comparison and evaluation. Not until after this comparison of data has been completed are specific surface unevennesses determined to be surface defects requiring reworking. A single extreme value of the surface defects indicated in the foregoing is generally not authoritative in determining the need for reworking.

Surface defects recognized as relevant by an inspector are recorded by metrologic means and stored in the computer system as defect patterns for compilation of a list of defects of this type. After subjective collection of a plurality of surface defects by an inspector and transfer of corresponding objectively acquired data defect patterns to the computer system, there is ultimately compiled in the latter a list of defect patterns which are objectively recognized by the measuring system in conjunction with the computer system.

The error recognition software is based on artificial intelligence techniques, which map surface defects in imprecise ("fuzzy") form, classify, and if necessary correct them. The strength of the fuzzy theory is utilized in solution of complex decision making problems. What are essential are the imprecise quantities, so-called fuzzy sets, factors which affect decision making, and the switching operation which permits continuous classification for evaluation.

In addition, adaptive software is used, so that new defect types can be simply supplemented as defect patterns or automatically constructed in an adaptation process. Artificial intelligence techniques make adaptivity of the system such as this possible. On the basis, for example, of surface defects recognized by an inspector the defects are quantified, analyzed, and classified. The quantity of examples assimilated contributes to increase in the body of knowledge, so that the system becomes increasingly intelligent. Creation of a system with artificial intelligence is subdivided into the partial steps of extraction of the characteristics of the surface defects, arrival at the design of the defect category, the adaptation phase, and, lastly, integration.

The typical surface defects of the body types are recorded during creation of the software. The characteristics of these surface defects are analyzed so that an approximate classification of the defect spectrum is obtained. Installation of the software is followed by the learning phase, in which the surface defects of a plurality of vehicle bodies are provisionally marked by various inspectors. The system receives the defects, analyzes them, and adds to the defect list of this type. Other vehicle bodies of the system are inspected and verified by the inspectors. Nonrelevant defects are marked again and transmitted to the system. This serves the purpose of optimizing the classification. As a result, new defect types can be assimilated after integration of the system. The defects are sorted by frequency, so that frequently occurring defects may be more rapidly recognized.

The position of recognized defects is forwarded by the computer after the recognition process to a marking device downstream from the measuring device. In the marking device a suitable mark is applied to the surface defect on the body shell by controllable marking nozzles in accordance with the defect coordinate data acquired. The marking is applied with water- soluble paint.

The surface defects as thus marked can be reworked by simple means in a process step downstream from the marking unit. As soon as a body shell has passed through the optical measuring device, the body shell following it is examined for surface defects in the same manner.

Online surface recognition under operating conditions and at the conveyor speeds employed in series production is made possible by the strip projection and evaluation of a test strip applied in this process and by use of a CCD camera.

Figure 2:
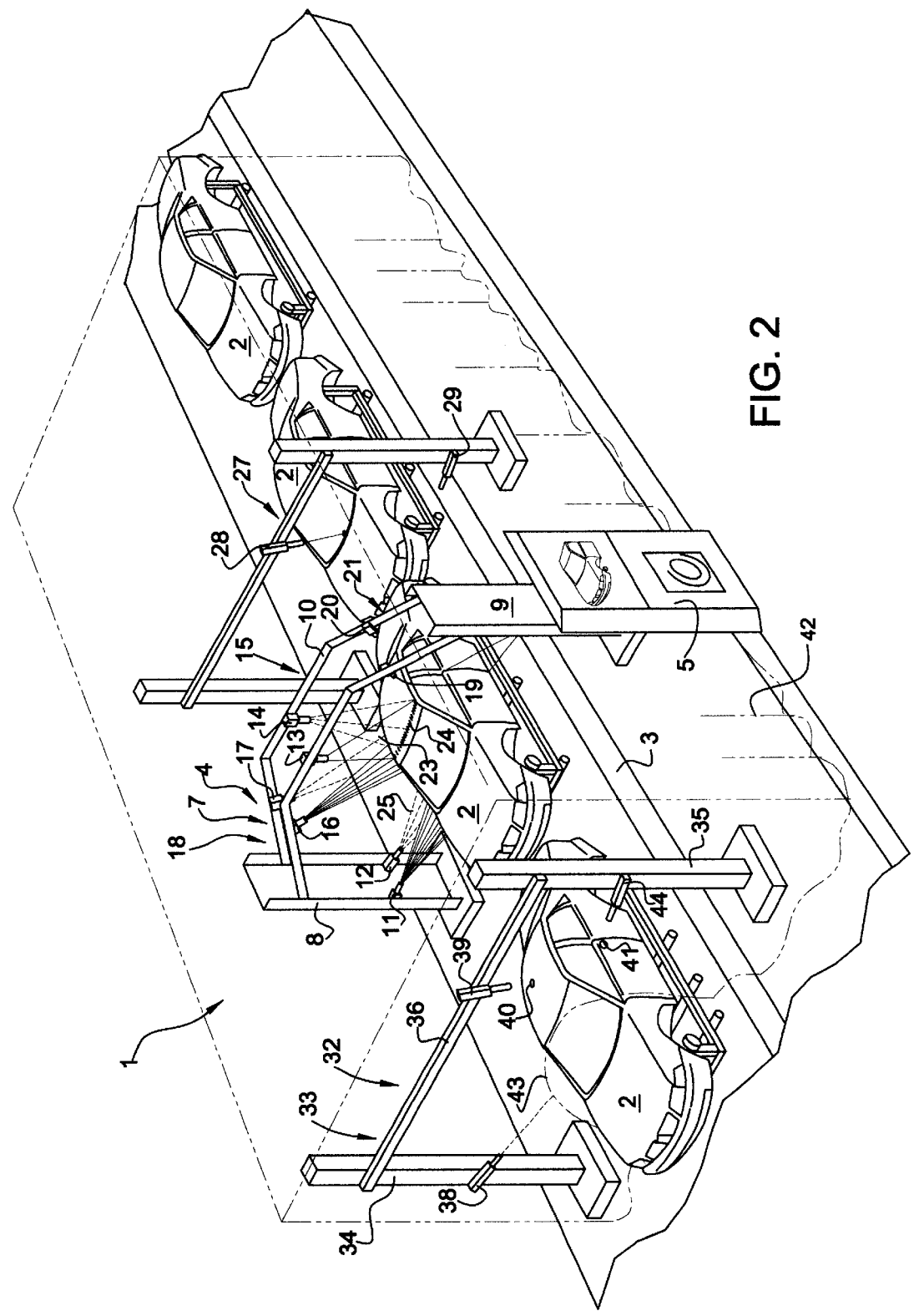
FIG. 2 an exploded view of a corresponding device.

An exploded view of a device 1 for application of a process for automatic recognition of surface defects on body shells 2 is illustrated in FIG. 2.

This device 1 comprises essentially a conveyor belt 3 for conveyance of body shells 2, a sensor system 27, an optical measuring device 4, a computer system 5, and a marking system 32.

Vibration-free and smooth passage of the body shell 2 through the optical measuring device 4 is necessary for accuracy of the optical measuring process. For this purpose the conveyor belt 3 is designed for continuous, stable, and smooth running and is movable by a small-link conveyor chain (not shown in the drawing).

Mounted upstream from the optical measuring device 4 is a sensor system 27 which comprises a sensor 29 for recognition of the beginning of the body shell 2 and a sensor 28 for acquisition of body data relating to a vehicle data carrier 30. These sensors 28, 29 are connected to the computer system 5, which is designed as an integrated computer system and processes large quantities of data in a short time. Specifically, the computer system 5 comprises a control computer, a measuring computer, and an evaluation computer interconnected in a network by fiber optic cables.

Adjoining the sensor system 27 in the direction of conveyance of the conveyor belt 3 is the optical measuring device 4. The latter surrounds the conveyor belt 3 transversely to the direction of conveyance of the latter with a gantry 7 as bearing structure. The gantry 7 comprises gantry uprights 8, 9 mounted on the two sides of the conveyor belt 3 and a vertically adjustable upper gantry crosspiece 10 controlled by the computer system 5 and mounted on the gantry uprights 8, 9.

A radiation emitter and a CCD camera associated with it, of which only the radiation emitter 11 and the CCD camera 12 on gantry upright 8 are shown in FIG. 2, are mounted on the gantry uprights 8, 9 for recognition of the lateral surfaces of the body shell 2 as it passes through the optical measuring device 4. For recognition of the top-view surfaces in the roof area, hood area, and trunk area of the body shell 2 area a radiation emitter 13 and an associated CCD camera 14 in a central area 15 of the gantry crosspiece 10 and a radiation emitter 16 or 19 and an associated CCD camera 17 or 20 are mounted in a side area 18, 21 of the gantry crosspiece 10 positioned at an angle to the center of the gantry 15.

Each of the radiation emitters 11, 13, 16, 19 and each of the associated CCD cameras 12, 14, 17, 20 are mounted at the same height on the gantry 7, each of radiation emitters 11, 13, 16, 19 being mounted so as to be offset in the direction of the body shell 2 ahead of the CCD cameras 12, 14, 17, 20. The radiation emitters 11, 13, 16, 19 and the CCD cameras 12, 14, 17, 20 are mounted pivotably on the gantry 7 so as to be controlled by the computer system 5.

The radiation emitters 11, 13, 16, 19 form a disk-shaped light tunnel 23 as a light curtain with a specific grid pattern of lighter and darker grid pattern points as measuring strip 24 on the surface of the body shell 2. The CCD cameras 12, 14, 17, and 20 record the light 25 reflected from the surface of the body shell 2 as an image of the grid points at a specific angle and emit a corresponding test signal which is forwarded to the computer system 5. Surface defects requiring reworking are determined in the computer system 5 by use of state-of-the-art triangulation methods, three-dimensional phase shifts being taken into account if desired.

A marking device 32 is mounted downstream from the optical measuring device 4. This marking device comprises a gantry 33 as bearing structure which consists of two gantry uprights 34, 35 each mounted laterally from the conveyor belt 2 and a vertically adjustable gantry crosspiece which rests on gantry uprights 34, 35 and is controlled by the computer system 5. Controlled- movement and replaceable marking nozzles 38, 39, 44 charged with water-soluble paint for marking relevant surface defects 40, 41 are mounted on the gantry 33. For the sake of precise defect position marking, a specific maximum spacing from the body shell must not be exceeded. Since the spacing of the lateral marking nozzles 38, 44 from the lateral surfaces of the body shell 2 always remains more or less the same, all that is required is body-outline-controlled spacing for the marking nozzle 39, which is for this purpose displaced vertically by the gantry crosspiece 36.

As is indicated only in diagrammatic form in FIG. 2, the device 1 is surrounded by an opaque curtain 42 as shielding from stray light. Openings 43 of suitable size are kept clear for this purpose in the entrance and exit areas of the body shells 2.

The conveyor belt 3, the optical measuring device 4, and the marking device 32 may be designed as a self-contained unit for the purpose of variable use of the device 1 as a whole. Such a device I is used preferably in the process chain between body shell fine finishing and base enameling.

We claim:

1. In a vehicle production process, a system for detecting selected surface defects of a vehicle body prior to painting, comprising:

a conveyor operative for advancing a plurality of said vehicle bodies along a line of travel;

an array of devices disposed transversely of said line of travel, operative to irradiate at selected angles, sequential transverse sections of each of said vehicle bodies with grid patterns of light;

a plurality of devices, operative to optically detect reflective grid patterns of light from said transverse sections;

a computer including a processor and a database provided with files of reference data representing relevant defect surfaces of selected vehicle bodies, operative to process data generated by said detecting devices, utilizing triangulation techniques and accounting for three dimensional phase shifts, to generate composite detected data, comparing said composite detected data with selected reference data to generate identification data representing coordinates of relevant defect surfaces of said vehicle bodies; and means operative in response to said identification data for marking relevant defect surfaces of said bodies.

2. A system according to claim 1 including means for detecting the presents of a vehicle body at a selected point along said line of travel and transmitting data representing said position to said computer.

3. A system according to claim 1 including means for identifying the configurations of said vehicle bodies and transmitting data representing said configurations to said computer.

4. A system according to claim 1 wherein the nature of said relevant defects includes at least one of depth, extent, frequency in occurrence, positioning and frequency in time.

5. A system according to claim 1 wherein said reference data comprises a compilation of defect surfaces visually determined by an operator.

6. A system according to claim 1 including means for editing said reference data to alter the composition of said relevant defect surfaces.

7. A system according to claim 1 wherein said marking means comprises at least one nozzle operative in response to command signals of said computer for training and ejecting a marker substance onto at least one relevant defect surface of a vehicle body as determined by said computer.

8. A system according to claim 7 wherein said marker substance comprises a water soluble material.

9. A method of detecting selected surface defects of a vehicle body comprising:

conveying a plurality of said vehicle bodies along a line of travel;

irradiating sequential transverse sections of said vehicle bodies at selected angles with grid patterns of light;

optically detecting reflective grid patterns of light from said transverse sections;

processing data representing said reflective grid patterns, utilizing triangulation techniques and accounting for three-dimensional phase shifts, to generate composite detected data, comparing said composite data with selected reference data representing relevant defect surfaces of selected vehicles bodies and generating identification data representing coordinates of relevant defect surfaces of said vehicles bodies; and marking relevant defect surfaces on said vehicle bodies responsive to said coordinates of said identification data.

10. A method according to claim 9 including detecting the presents of a vehicle body at a selected point along said line of travel and transmitting data representing said position to means for processing said data.

11. A method according to claim 9 including identifying the configurations of said vehicles bodies and transmitting data representing said configurations to means for processing said data.

12. A method according to claim 9 including editing said reference data to alter the composition of said relevant defect surfaces.

13. A method according to claim 9 including ejecting a substance on surface areas of said vehicle bodies corresponding to relevant defect surfaces as determined by said data processing.

* * * * *

UNITED STATES PATENT AND TRADEMARK OFFICE
CERTIFICATE OF CORRECTION

PATENT NO. : 6,320,654 B1
DATED : November 20, 2001
INVENTOR(S) : Klaus Alders, Martina Lehe and Gang Wan It is certified that error appears in the above-identified patent and that said Letters Patent is hereby corrected as shown below:

Column 9,
Line 8, delete "a vehicle body" insert -- vehicle bodies --
Line 32, delete "presents" insert -- presence --

Column 10,
Line 9, delete "a vehicle body" insert -- vehicle bodies --
Line 28, delete "presents" insert -- presence --
Line 32, delete "vehicles" insert -- vehicle --

Signed and Sealed this

Sixteenth Day of July, 2002

Attest:

JAMES E. ROGAN
Attesting Officer　Director of the United States Patent and Trademark Office